United States Patent [19]

Suga

[11] Patent Number: 5,648,221

[45] Date of Patent: Jul. 15, 1997

[54] OPTICAL INSPECTION METHOD

[75] Inventor: Takayuki Suga, Tsukuba, Japan

[73] Assignee: Nikon Corporation, Japan

[21] Appl. No.: 259,770

[22] Filed: Jun. 14, 1994

[30] Foreign Application Priority Data

| Jun. 14, 1993 | [JP] | Japan | 5-141708 |
| Jun. 14, 1993 | [JP] | Japan | 5-141709 |
| Jun. 14, 1993 | [JP] | Japan | 5-141710 |

[51] Int. Cl.⁶ ............... G01N 33/53; G01N 33/569
[52] U.S. Cl. ............ 435/7.21; 435/7.2; 435/7.23; 435/7.24; 435/808; 435/968; 436/164; 436/172; 436/800; 436/805; 436/813
[58] Field of Search ................... 435/7.2, 7.21, 435/7.23, 7.24, 808, 968; 436/164, 172, 800, 805, 813

[56] References Cited

U.S. PATENT DOCUMENTS

| 4,495,293 | 1/1985 | Shaffar ........................... 436/172 |
| 4,587,223 | 5/1986 | Soini et al. ....................... 436/536 |

FOREIGN PATENT DOCUMENTS

| 4-132020 | 5/1992 | Japan . |
| 4-269644 | 9/1992 | Japan . |
| 5-273129 | 10/1993 | Japan . |
| 6-138027 | 5/1994 | Japan . |

OTHER PUBLICATIONS

Optics Letters, vol. 16, No. 1, Jan. 1991, pp. 10–12, "Phase Modulation Technique For Accumulated Photon Echo Whole Document" by Saikan et al.

Optics Letters, vol. 16, No. 1, Jan. 1991, pp. 13–14, "Fluorescence Detection of Femtosecond Accumulated Photon Echo Whole Document" by Uchikawa et al.

Physical Review B, vol. 45, No. 22, Jun. 1, 1992, pp. 12752–12759, "Stimulated Photon Echo Spectroscopy" by Yano et al.

Journal of the Optical Society of America B, vol. B9, No. 6, Jun. 1992, pp. 941–945, "Ultrafast Dephasing of Resorufin, etc.", by Gruzdev et al.

Journal of Optical Society of America B, vol. B9, No. 6, Jun. 1992, pp. 987–991, "Spectral Hole Burning, etc.", by Bernet et al.

Applied Spectroscopy, vol. 45, No. 6, Jul. 1991, pp. 1041–1045, "Three Dimensional Space and Time Resolved Fluorescence Spectroscopy", by Sasaki et al.

Optics Letters, vol. 16, No. 21, Nov. 1991, pp. 1683–1685, "Femtosecond Time Resolved Interferometry" by Minoshima et al.

Primary Examiner—James C. Housel
Assistant Examiner—Christopher L. Chin
Attorney, Agent, or Firm—Pennie & Edmonds LLP

[57] ABSTRACT

Various methods for precisely inspecting presence or absence of an antigen-antibody reaction or a type of the antigen-antibody reaction are provided. A method comprises a first step of mixing an object to be inspected with a photosensitive material, a second step of mixing a mixture obtained in the first step with an antibody, and a third step of detecting a photon echo from a specimen obtained in the second step to examine presence or absence, or a type of an antigen-antibody reaction. A further method comprises a first step of mixing an object to be inspected with an antibody, a second step of mixing a secondary antibody for the antibody with a photosensitive material, a third step of mixing a mixture obtained in the first step with a mixture obtained in the second step, and a fourth step of detecting a photon echo from a specimen obtained in the third step to examine presence or absence, or a type of an antigen-antibody reaction. A further method comprises a first step of mixing an antibody with a photosensitive materials a second step of mixing an object to be inspected with a mixture obtained in the first step, and a third step of detecting a photon echo from a specimen obtained in the second step to examine presence or absence, or a type of an antigen-antibody reaction. A still further method comprises a first step of mixing an object to be inspected with an antibody, a second step of mixing a mixture obtained in the first step with a photosensitive material, and a third step of detecting a photon echo from a specimen obtained after completion of the second step to examine presence or absence, or a type of an antigen-antibody reaction.

19 Claims, 6 Drawing Sheets

OPTICAL INSPECTION METHOD

BACKGROUND OF THE INVENTION

1. Field of the Invention

The present invention relates to a method for optically inspecting presence or absence of an antigen-antibody reaction in a specimen or a type of an antigen-antibody reaction in a specimen by measuring a photon echo from the specimen.

2. Related Background Art

An antigen-antibody reaction has been used in inspection for various diseases, utilizing its extremely unique specificity. Heretofore, various methods have been developed for inspection of the antigen-antibody reaction.

For example, there are methods using an antibody labelled with a fluorescent material (a kind of probe) (fluorescent antibody). The methods are classified into (1) a direct method in which an antibody is preliminarily labelled with a fluorescent material (to obtain a labelled antibody), and then the labelled antibody is mixed (reacted) with an antigen; and (2) an indirect method in which an antigen is mixed (reacted) with an antibody (primary antibody), and then the mixture is further mixed with a secondary antibody labelled with a fluorescent material.

A specimen as so mixed (reacted) is observed with a fluorescence microscope, and presence or absence of an antigen-antibody reaction or a type of an antigen-antibody reaction is determined from its fluorescence amount or its fluorescence pattern. Further, for the case that an antigen is reacted with a corresponding antibody to agglutinate, there is a method in which presence or absence of an antigen-antibody reaction is determined by examining its reaction pattern, i.e., a degree of the aggregation.

However, in the conventional methods as described above, an observer observes the specimen with the naked eye or through a microscope. Therefore, there are such problems that judgement can hardly be made and that objective judgement cannot be made, because the judgement depends on an individual to make it.

SUMMARY OF THE INVENTION

The present invention has been accomplished in view of the above problems and provides a method for objectively and precisely inspecting presence or absence of an antigen-antibody reaction or a type of an antigen-antibody reaction. The present inventors have conducted extensive and intensive research to solve the above problems. As a result, it was found that presence or absence of an antigen-antibody reaction or, a type or a degree of an antigen-antibody reaction could be detected by measuring a photon echo from a specimen and examining information obtained therefrom (e.g., a phase relaxation time ($T_2$), an intensity of the photon echo (including presence or absence of photon echo), a ratio of an intensity of the photon echo originated from a zero phonon line to an intensity of the photon echo originated from a phonon side band, etc.). The present invention is based on the above finding.

An inspection method of the present invention comprises a first step of mixing an object to be inspected with a photosensitive material, a second step of mixing a mixture obtained in the first step with an antibody, and a third step of detecting an photon echo from a specimen obtained in the second step to examine presence or absence, or a type of an antigen-antibody reaction.

Another inspection method of the present invention comprises a first step of mixing an object to be inspected with an antibody, a second step of mixing a secondary antibody for the antibody with a photosensitive material, a third step of mixing a mixture obtained in the first step with a mixture obtained in the second step, and a fourth step of detecting a photon echo from a specimen obtained in the third step to examine presence or absence, or a type of an antigen-antibody reaction.

A further inspection method of the present invention comprises a first step of mixing an antibody with a photosensitive material, a second step of mixing an object to be inspected with a mixture obtained in the first step, and a third step of detecting a photon echo from a specimen obtained in the second step to examine presence or absence, or a type of an antigen-antibody reaction.

A still further inspection method of the present invention comprises a first step of mixing an object to be inspected with an antibody, a second step of mixing a mixture obtained in the first step with a photosensitive material, and a third step of detecting a photon echo from a specimen obtained after completion of the second step to examine presence or absence, or a type of an antigen-antibody reaction.

Further, "mixing" and "mixture" in meaning above is "to blend some materials physically", "to react some materials physico-chemically", "to combine some materials physico-chemically", "to give a colour to some materials by means of dye" or "to label a labelling reagent to some materials physico-chemically".

A photon echo is extremely sensitive to a difference in the structure, in the constituent, or the like, so that the difference in the physicochemical properties appears as a difference in the phase relaxation time ($T_2$) in the inspection according to the present invention as described above. Accordingly, a name (kind) of an object to be inspected or a state thereof can be determined by measuring the phase relaxation time ($T_2$).

DESCRIPTION OF THE PREFERRED EMBODIMENTS

Figure 1:
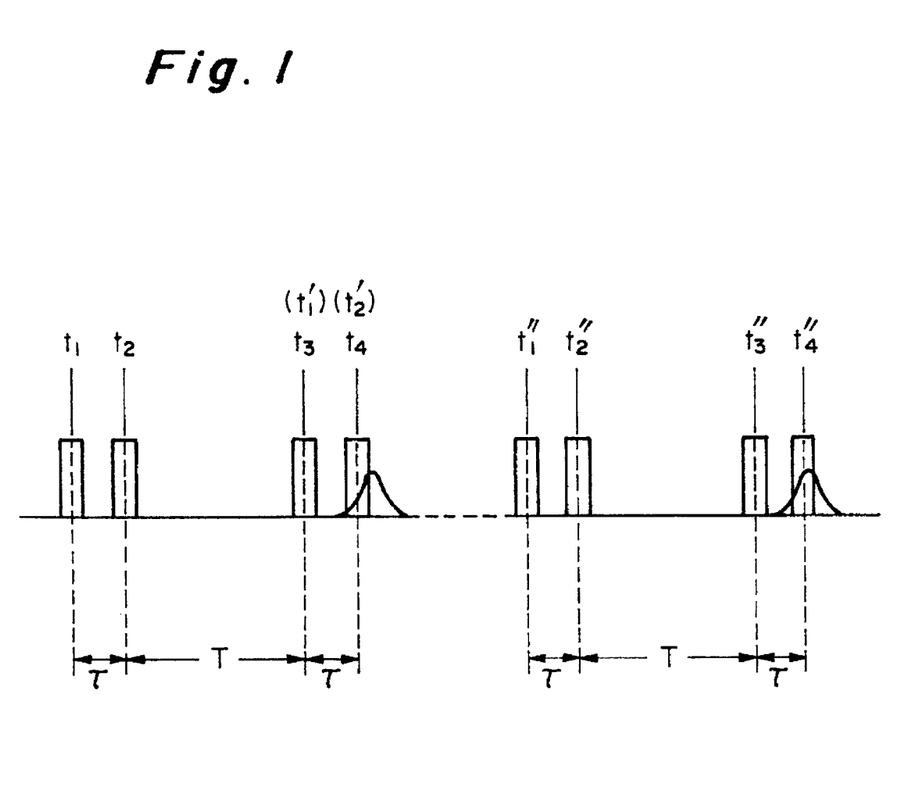
FIG. 1 is a drawing to show the principle of conventional photon echo measurement.

First described referring to FIG. 1 is the principle to clarify how to determine a physicochemical property by measuring an optical phase relaxation time with a photon echo.

Here, let us consider an example of phase relaxation time ($T_2$), in which a material to be measured is excited by a pulse beam (excitation light).

In FIG. 1, a pulse beam of $E_1$ is irradiated at time $t_1$, and subsequently a pulse beam of $E_2$ is irradiated at time $t_2$. Then, when a pulse beam of $E_3$ is irradiated at time $t_3$, the material in turn emits a beam at time of $[t_3+t_2-t_1=t_3+\tau(\tau=t_2-t_1)]$. The emitted beam is a photon echo. The intensity of the photon echo decays in proportion to $\exp(-4\tau/T_2)$. Varying the interval $\tau$ and measuring the intensity of photon echo for each interval, $T_2$ can be determined. The phase relaxation time $T_2$ changes depending on a material or on a state of the material. Accordingly, once the phase relaxation time $T_2$ is obtained, the material or the state of material can be determined. This measuring method is disclosed in detail in Japanese Laid-open Patent Application No. 4-132020.

The present invention utilizes this photon echo.

In order to measure a photon echo, a specimen must have absorption at the wavelength of excitation light (generally, a laser beam). Namely, a material to be measured (a specimen) must be a light absorber for the excitation light. Generally speaking, a specimen to be examined with respect to an antigen-antibody reaction, has no absorption for light with wavelengths in the visible region. At present, there exists no laser for measuring the photon echo, having a wavelength in the ultra-violet region, so that the above-described specimen can show no absorption with the excitation light. Thus, in the present invention, a photosensitive material having absorption at the wavelength of excitation light is preliminarily mixed with an object to be inspected. The mixture becomes a light absorber for the wavelength of excitation light, whereby a photon echo can be measured.

Hereinafter, a plurality of embodiments according to the present invention will be described, but it should be noted that the present invention is by no means restricted to these specific embodiments.

EMBODIMENT 1

Figure 2:
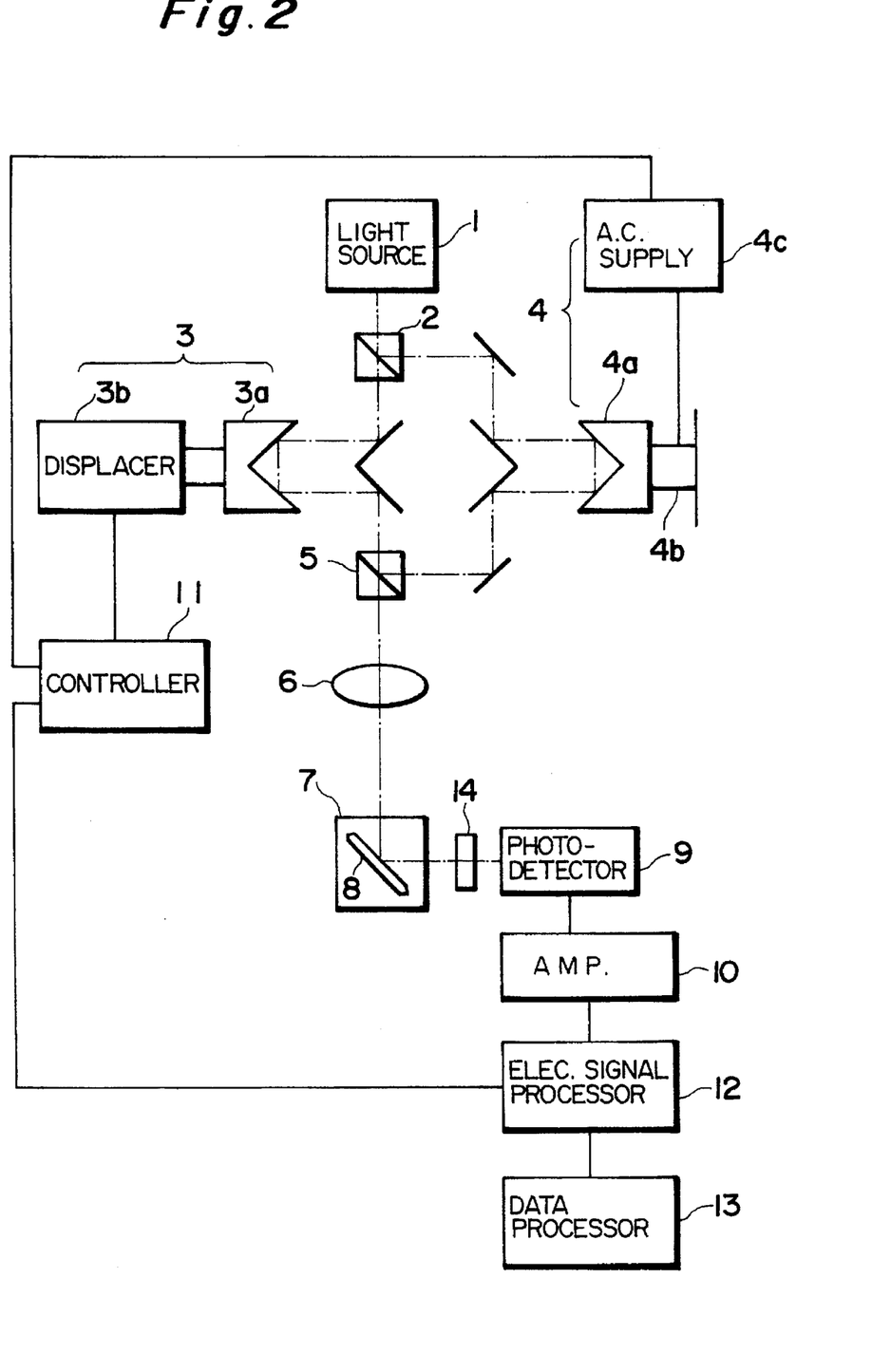
FIG. 2 is an explanatory illustration to show the structure of a photon echo measuring apparatus used in Embodiments of the present invention.

FIG. 2 is a drawing to show the structure of a photon echo measuring apparatus for measuring a photon echo from a specimen, which was proposed in the present applicant's Japanese Patent Application No. 4-284701.

In this photon echo measuring apparatus, a measurement optical system comprises a light source 1, a beam splitter 2, an optical delay unit 3 having a corner cube 3a and a displacer 3b, a phase modulation unit 4 having a corner cube 4a, a piezoelectric device 4b and an AC drive supply 4c, an optical mixer 5, a lens 6, a cooler 7, a photodetector 9, a locking amplifier 10, a control unit 11, an electric signal processing unit 12, a data processing unit 13, and a filter 14 as constituents. Further, a specimen is indicated as numeral 8.

The light source 1 supplies to the specimen light having spatial coherence and predetermined temporal coherence, specifically temporal coherence shorter than the optical phase relaxation time of a watched light absorber. The light source 1 comprises, for example, a dye laser pumped by a mode-locked argon ion laser. The optical delay unit 3 comprises the corner cube 3a fixed on an unrepresented movable stage and the displacer 3b which displaces the movable stage, whereby light is delayed while changing the position of corner cube 3a.

The phase modulation unit 4 comprises the corner cube 4a, the piezoelectric device 4b and the AC drive supply 4c. One end of the piezoelectric device 4b is fixed while to the other end of the piezoelectric device 4b, the corner cube 4a is fixed. In the phase modulation unit 4, the piezoelectric device 4b vibrates at frequency f when an AC voltage with predetermined frequency f is applied to the piezoelectric device 4b from the AC drive supply 4c. Further, the corner cube 4a is vibrated at frequency f with the vibration of piezoelectric device 4b. The vibration of the corner cube 4a modulates the phase of light by the frequency f. In Embodiment 1, the phase modulation frequency was set to 21 kHz.

The photodetector 9 is an optical multiplier phototube (photomultiplier). The sharp cut filter 14 transmits only light having wavelengths longer than that of the irradiated laser beam. The lockin amplifier 10 is a signal processing unit to extract a modulation component having a frequency equal to the double of the modulation frequency of the phase modulation unit 4. In Embodiment 1, the lockin frequency of lockin amplifier 10 was set to 42 kHz to detect an photon echo.

The light emitted from the light source 1 is split into two beams by the beam splitter 2. The optical delay unit 3 is arranged on the transmission beam path of the light beam splitter 2 in order to produce a predetermined amount of optical delay. Further, the phase modulation unit 4 is arranged on the reflection beam path of splitter 2 in order to produce a predetermined amount of phase modulation. The light delay unit 3 and the phase modulation unit 4 are controlled by the control unit 11. The two beams passing through the light delay unit 3 and the phase modulation unit 4, respectively, are mixed by the optical mixer 5 to form a mixed beam.

The mixed beam by the optical mixer 5 is then condensed through the lens 6 onto the specimen in the cooler 7. The lens 6 may be replaced by an optical system in a microscope which is arranged to condense light while observing the specimen. A photon echo from the specimen is detected by the photodetector 9 through the sharp cut filter 14. An output signal from the photodetector 9 is processed by the lockin amplifier 10. An output signal of the lockin amplifier 10 is transmitted to the data processing unit 13 through the electric signal processing unit 12.

The phase relaxation time ($T_2$) of the specimen can be obtained by recording a change in intensity of photon echo as caused when the optical path difference between the two optical beams is consecutively changed by the optical delay unit.

Figure 5:
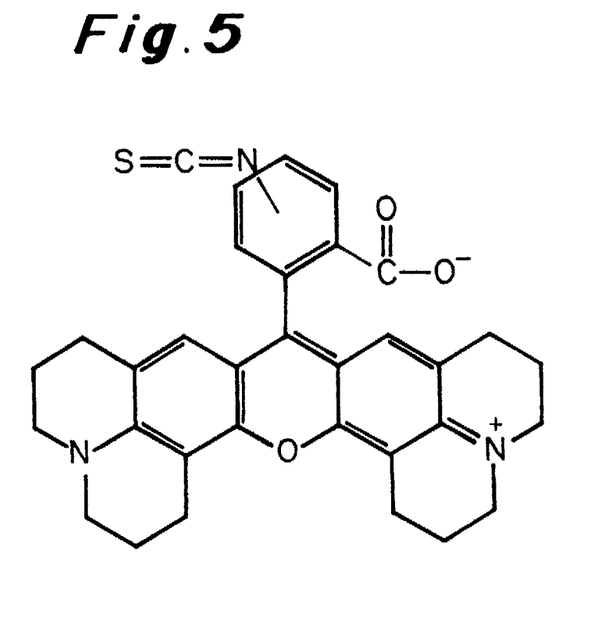
FIG. 5 is a drawing to show the chemical formula of XRITC.

As an object to be inspected (inspected object), a cultured cell of human-laryngeal-cancer (HEp-2) was used. As the antibody, an anti-nucleolus antibody and an anti-DNA antibody contained in blood serum were used. The cultured cell of human-laryngeal-cancer (HEp-2) was mixed with XRITC, which is a staining dye (photosensitive material). This mixture was then mixed with either of the above antibodies. Each of the specimens thus obtained was inspected. The chemical formula of XRITC is shown in FIG. 5.

The two types of specimens were inspected by the accumulated photon echo measuring apparatus as described above, and they were able to be clearly distinguished from each other by a difference in the phase relaxation time ($T_2$). Namely, the difference was able to be distinguishably recognized between the two types of antigen-antibody reactions.

The same results were obtained by measuring of the another type of the photon echo, i.e., two-pulse photon echo, stimulated photon echo.

Figure 6:
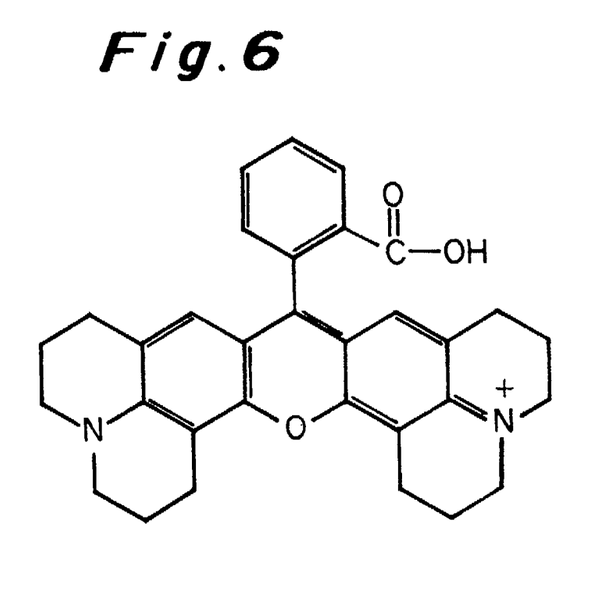
FIG. 6 is a drawing to show the chemical formula of rhodamine 640.
Figure 7:
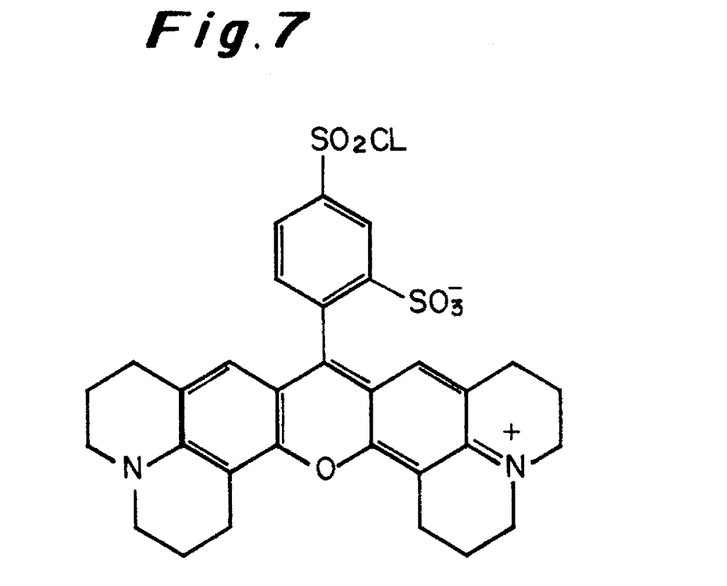
FIG. 7 is a drawing to show the chemical formula of Texas red.
Figure 8:
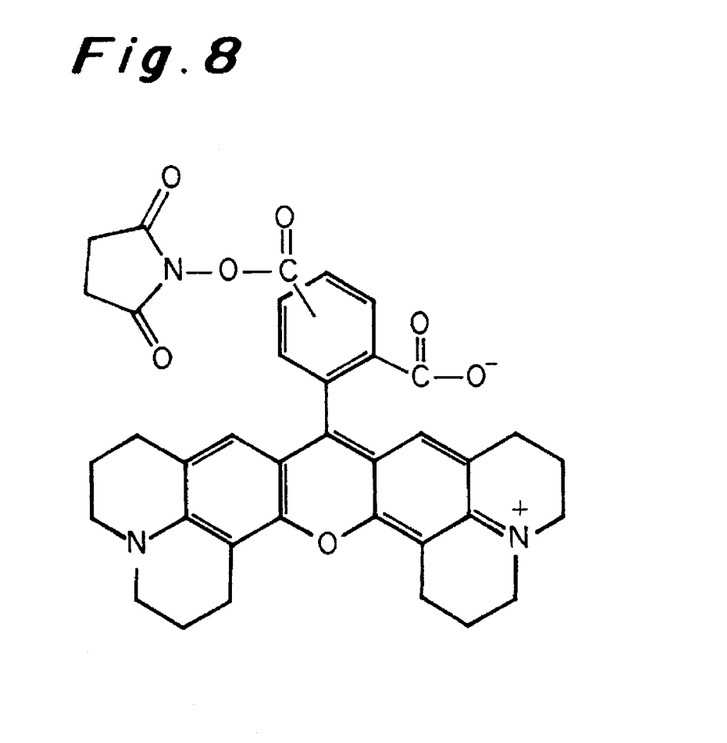
FIG. 8 is a drawing to show the chemical formula of 5(6) carboxy-x-rhodamine succinimidyl ester.

The same results were obtained in case rhodamine x derivative, i.e., rhodamine 640, Texas red, or 5(6) carboxy-x-rhodamine succinimidyl ester was used as the staining dye (photosensitive material). The chemical formula of rhodamine 640 is shown in FIG. 6. The chemical formula of Texas red is shown in FIG. 7. Further, the chemical formula of 5(6) carboxy-x-rhodamine succinimidyl ester is shown in FIG. 8.

As the photosensitive material, any kinds of materials can be used as long as a photon echo of the material can be observed. For example, an enzyme may be employed. In case of an enzyme being used, after mixing the enzyme in the inspected object, a chemical is further mixed thereinto so that the mixture thus obtained can become a light absorber for the excitation light.

In Embodiment 1, the apparatus as described above was used for measuring the photon echo. However, the present invention is by no means limited to the specific apparatus as long as the photon echo can be measured.

EMBODIMENT 2

Figure 3:
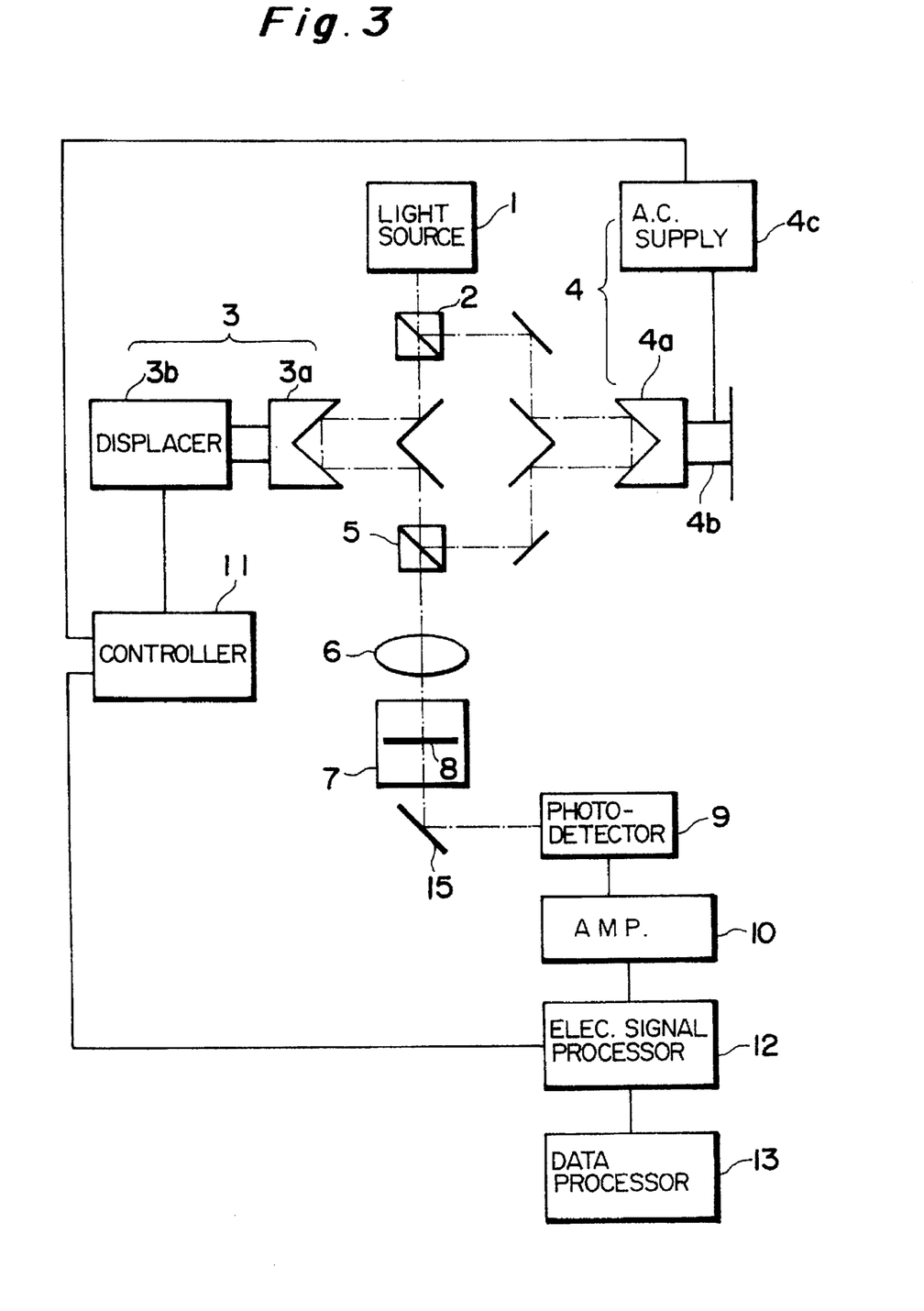
FIG. 3 is an explanatory illustration to show the structure of another photon echo measuring apparatus used in Embodiments of the present invention.

FIG. 3 is a drawing to show a photon echo measuring apparatus proposed in the present applicant's Japanese Patent Application No. 4-98643. In FIG. 3, constituents which are the same as or equivalent to those in FIG. 2 are denoted by the same reference numerals.

A difference between the apparatus of Embodiments 1 and 2 resides in that a beam transmitted through a specimen is detected by the photodetector 9 in the apparatus of Embodiment 2.

Specimens obtained in the same treatment as in Embodiment 1 were inspected using the apparatus, and they were able to be distinguished from each other as in Embodiment 1. Namely, the difference was able to be distinguishably recognized between the two types of the antigen-antibody reactions.

Further, in case the specimens had a very strong scattering property, the scattered light was collected and condensed with lens and the condensed light was then detected by the photodetector 9, whereby they could be distinguished similarly from each other.

EMBODIMENT 3

Figure 4:
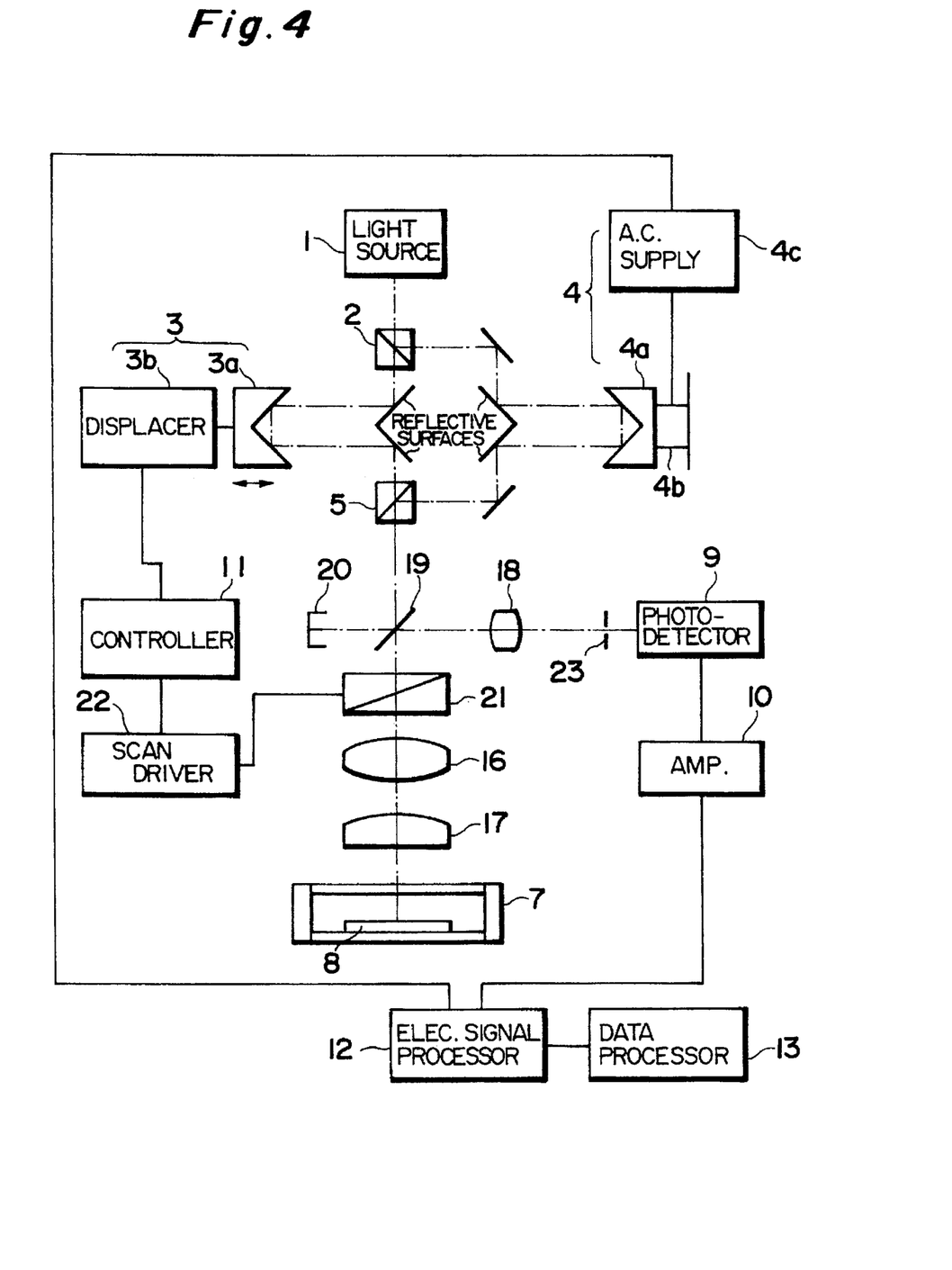
FIG. 4 is an explanatory illustration to show the structure of another photon echo· measuring apparatus used in Embodiments of the present invention.

FIG. 4 is a drawing to show a photon echo measuring apparatus proposed in the present applicant's Japanese Laid-open Patent Application No. 4-269644. In FIG. 4, constituents which are the same as or equivalent to those in FIG. 2 or FIG. 3 are denoted by the same reference numerals.

This apparatus has the same arrangement as a confocal laser scanning microscope, and only light passing through a pinhole 23 located at the confocal position with the focal position on the specimen, is detected by the photodetector. Namely, the photon echo measuring apparatus in Embodiment 3 further comprises objective lenses 16, 17, a lens 18, a semi-transparent mirror 19, an optical trap 20, a scanning unit 21 and a scanning drive unit 22.

Specimens obtained in the same treatment as in Embodiment 1, were inspected using the above apparatus, and they were able to be distinguished from each other as in Embodiment 1. Namely, the difference was able to be distinguishably recognized between the two types of the antigen-antibody reactions.

EMBODIMENT 4

As the inspected object, a cultured cell of human-laryngeal-cancer (HEp-2) was used. As blood serum, that containing an antinuclear antibody and that containing no antinuclear antibody were used. The above inspected object was mixed with XRITC, which is an orthochromatic dye for cell (photosensitive material). Then, either of the above two types of blood serum was then mixed with the mixture. Each of the specimens thus obtained were inspected.

These specimens were inspected as to a photon echo in the same manner as in Embodiments 1, 2 and 3, and they were able to be clearly distinguished from each other by a difference in the phase relaxation time ($T_2$) thereof.

Namely, the difference was able to be distinguishably recognized between presence and absence of the antigen-antibody reaction.

EMBODIMENT 5

As the inspected object, a cultured cell of human-laryngeal-cancer (HEp-2) was used. As the antibody, an anti-DNA antibody and an antinuclear corpuscle antibody contained in blood serum were used.

A secondary antibody for the anti-DNA antibody or the anti-nucleolus antibody was preliminarily mixed with XRITC, which is a staining dye (photosensitive material). Each of the above two antibodies was then mixed to the cultured cell of human-laryngeal-cancer (HEp-2). Then, either of the mixtures was mixed with the secondary antibody preliminarily mixed with XRITC. Each of the specimens thus obtained was inspected using the photon echo measuring apparatus as described in Embodiment 1, 2, or 3. The specimens were able to be clearly distinguished from each other by a difference in the phase relaxation time ($T_2$) thereof. Namely, the difference was able to be distinguishably recognized between the two types of the antigen-antibody reactions.

Further, the same results were obtained when rhodamine x derivative, i.e., rhodamine 640, Texas red, or 5(6) carboxy-x-rhodamine succinimidyl ester was used as the photosensitive material.

As the photosensitive material, any kinds of materials can be used as long as the photon echo of the material can be observed. For example, an enzyme may be employed. In case of an enzyme being used, after mixing the enzyme in the inspected object, a chemical is further mixed thereinto so that the mixture thus obtained can become a light absorber for the excitation light.

In Embodiment 5, the apparatus as described above in Embodiments 1, 2 and 3 were used for measuring the photon echo. However, the present invention is by no means limited to the specific apparatus as long as the photon echo can be measured.

EMBODIMENT 6

As the inspected object, a cultured cell of human-laryngeal-cancer (HEp-2) was used. As the antibody, an antinuclear antibody contained in blood serum, and an antibody contained in blood serum, which was not an antibody for the cultured cell of human laryngealcamcei (HEp-2), were used.

A secondary antibody for each of the above two antibodies was preliminarily mixed with XRITC, which is photosensitive material. The above inspected object was mixed with either of the two types of antibodies. Then, each of the mixtures thus obtained was mixed with the second antibody mixed with XRITC. Each of the specimens thus obtained was inspected.

These specimens were inspected with the same photon echo measuring apparatus as described in Embodiment 1, 2 or 3. Because no photosensitive material was present in the specimen which did not contain the antibody for the cultured cell of human-laryngeal-camcei (HEp-2), no photon echo was measured. On the other hand, a photon echo was measured from the specimen containing the antinuclear antibody. Accordingly, these specimens were able to be clearly distinguished from each other by presence or absence of photon echo.

Namely, the difference was able to be distinguishably recognized between presence and absence of the antigen-antibody reaction.

EMBODIMENT 7

As the inspected object, a cultured cell of human-laryngeal-cancer (HEp-2) was used. As the antibody, an anti-DNA antibody and an anti-nucleolus antibody contained in blood serum were used.

Each of the above two antibodies was preliminarily "mixed" with XRITC, which is a photosensitive material. Then, cultured cell of human-laryngeal-cancer (HEp-2) was mixed with either of the antibodies mixed with XRITC. Each of the specimens thus obtained was inspected.

These specimens were inspected using the same photon echo measuring apparatus as in Embodiment 1, 2 or 3, and they were able to be clearly distinguished from each other by a difference in the phase relaxation time ($T_2$) thereof, as in Embodiment 1, 2 or 3. Namely, the difference was able to be distinguishably recognized between the two types of antigen-antibody reactions.

EMBODIMENT 8

As the inspected object, a cultured cell of human-laryngeal-cancer (HEp-2) was used. As the antibody, an antinuclear antibody contained in blood serum, and an antibody contained in blood serum, which was not an antibody for the cultured cell of human-laryngeal-cancer (HEp-2) (the antinuclear antibody), were used.

Each of the above two antibodies was preliminarily mixed with XRITC, which is staining dye (photosensitive material). Then, cultured cell of human-laryngeal-cancer (HEp-2) was mixed with either of the antibodies mixed with XRITC. Each of the specimens thus obtained was inspected.

These specimens were inspected using the same photon echo measuring apparatus as in Embodiment 1, 2 or 3. Because no photosensitive material existed in the specimen which did not contain the antibody for the cultured cell of human-laryngeal-cancer (HEp-2), no photon echo was measured. On the other hand, a photon echo was measured from the specimen containing the antinuclear antibody. Accordingly, these specimens were able to be clearly distinguished from each other by presence or absence of the photon echo.

Namely, the difference was able to be distinguishably recognized between presence and absence of the antigen-antibody reaction.

EMBODIMENT 9

As the inspected object, a cultured cell of human-laryngeal-cancer (HEp-2) was used. As blood serum that containing an antinuclear antibody and that containing no antinuclear antibody were used. The above inspected object was mixed with either of the two types of blood sera. Then, each of the two mixtures was mixed with XRITC, which is a staining dye (photosensitive material). Each of the specimens thus obtained was inspected.

These specimens were inspected using the above accumulated photon echo measuring apparatus, and they were able to be clearly distinguished from each other by a difference in the phase relaxation time ($T_2$) thereof. Namely, the difference was able to be distinguishably recognized between presence and absence of the antigen-antibody reaction.

The same results were obtained by measuring of the another type of the photon echo, i.e., two-pulse photon echo, stimulated photon echo.

Further, the same results were obtained when rhodamine x derivative, i.e., rhodamine 640, Texas red or 5(6) carboxy-x-rhodamine succinimidyl ester was used as the orthochromatic dye for cell (photosensitive material).

As the photosensitive material, any kinds of materials can be used as long as the photon echo of the material can be observed. For example, an enzyme may be employed. In case of an enzyme being used, after mixing the enzyme in the inspected object, a chemical is further mixed thereinto so that the mixture thus obtained can become a light absorber for the excitation light.

In Embodiment 9, the apparatus as described previously were used for measuring the photon echo. However, the present invention is by no means limited to the specific apparatus as long as the photon echo can be measured.

EMBODIMENT 10

As the inspected object, a cultured cell of human-laryngeal-cancer (HEp-2) was used. As the antibody, an anti-DNA antibody and an anti-nucleolus antibody contained in blood serum were used.

The cultured cell of human-laryngeal-cancer (HEp-2) was mixed with either of the two types of antibodies. Then, each of the two types of mixtures thus obtained was mixed with XRITC, which is staining dye (photosensitive material). Each of the specimens thus obtained was inspected.

These specimens thus obtained were inspected using the same photon echo measuring apparatus as in Embodiment 1, 2 or 3, and they were able to be clearly distinguished from each other. Namely, the difference was able to be distinguishably recognized between the two types of the antigen-antibody reactions.

The present invention provides inspection methods which can detect presence or absence of an antigen-antibody reaction, or a type of the antigen-antibody reaction, as illustrated with the typical cases in Embodiment 1 to Embodiment 10. By using the methods of the present invention, inspection results of the antigen-antibody reaction, which used to rely on observation with observer's naked eye or through a microscope, can be shown objectively with numerical values, realizing precise examination.

What is claimed is:

1. A method for optically determining the presence or absence of an antigen-antibody reaction comprising:

a first step of mixing an object having an antigen with a photosensitive material that binds to said object;

a second step of mixing a mixture obtained in said first step with an antibody that specifically binds to said antigen; and a third step of applying an excitation light to a specimen obtained in said second step to emit a photon echo and examining the photon echo to determine the presence or absence of said antigen-antibody reaction.

2. An optical inspection method according to claim 1, wherein said object to be inspected is a cultured cell.

3. An optical inspection method according to claim 1, wherein said antibody is contained in blood serum.

4. An optical inspection method according to claim 1, wherein said object to be inspected is an organism tissue.

5. A method for optically determining the presence or absence of an antigen-antibody reaction comprising:
   a first step of mixing an object having an antigen with a primary antibody that specifically binds to said antigen;
   a second step of mixing a secondary antibody with a photosensitive material that binds to said primary antibody;
   a third step of mixing a mixture obtained in said first step with a mixture obtained in said second step; and
   a fourth step of applying an excitation light to a specimen obtained in said third step to emit a photon echo and examining the photon echo to determine the presence or absence of said antigen-antibody reaction.

6. An optical inspection method according to claim 5, wherein said object to be inspected is a cultured cell.

7. An optical inspection method according to claim 5, wherein said antibody is contained in blood serum.

8. An optical inspection method according to claim 5, wherein said object to be inspected is an organism tissue.

9. A method for optically determining the presence or absence of an antigen-antibody reaction comprising:
   a first step of mixing an antibody with a photosensitive material;
   a second step of mixing an object having an antigen with a mixture obtained in said first step; and
   a third step of applying an excitation light to a specimen obtained in said second step to emit a photon echo and examining the photon echo to determine the presence or absence of said antigen-antibody reaction.

10. An optical inspection method according to claim 9, wherein said object to be inspected is a cultured cell.

11. An optical inspection method according to claim 9, wherein said antibody is contained in blood serum.

12. An optical inspection method according to claim 9, wherein said object to be inspected is an organism tissue.

13. A method for optically determining the presence or absence of an antigen-antibody reaction comprising:
   a first step of mixing an object having an antigen with an antibody that specifically binds to said antigen;
   a second step of mixing a mixture obtained in said first step with a photosensitive material that binds to said object; and
   a third step of applying an excitation light to a specimen obtained after completion of said second step to emit a photon echo and examining the photon echo to determine the presence or absence of said antigen-antibody reaction.

14. An optical inspection method according to claim 13, wherein said object to be inspected is a cultured cell.

15. An optical inspection method according to claim 13, wherein said antibody is contained in blood serum.

16. An optical inspection method according to claim 13, wherein said object to be inspected is an organism tissue.

17. A method for optically determining the presence or absence of an antigen-antibody reaction comprising the steps of:
   (a) irradiating first, second and third excitation light pulses at first, second and third times, respectively, into a specimen which is comprised of an antigen-antibody complex labeled by a photosensitive material that binds to said complex, said excitation light pulses generating a photon echo from said specimen; and
   (b) detecting the intensity of said photon echo to provide an indication of the presence or absence of said antigen-antibody reaction.

18. A method according to claim 17, wherein a plurality of sets of said steps (a) and (b) are performed so that time differences, $\tau$, between said first and second times at which said excitation light pulses are irradiated into said specimen are varied form one set to the next, and said method further comprising the step of:
   measuring the respective intensities of said photon echoes detected at said respective time differences $\tau$; and
   evaluating said specimen by using a unique constant calculated for said specimen, said unique constant being calculated based on said time differences $\tau$ and said intensities of said photon echoes.

19. A method according to claim 18, wherein said unique constant is a phase relaxation time of said specimen.

* * * * *